(12) United States Patent
Helming et al.

(10) Patent No.: US 6,996,208 B2
(45) Date of Patent: Feb. 7, 2006

(54) X-RAY OPTICAL SYSTEM WITH WOBBLE DEVICE

(75) Inventors: Kurt Helming, Dresden (DE); Lutz Brügemann, Durmersheim (DE)

(73) Assignee: Bruker Axs GmbH, Karlsruhe (DE)

( * ) Notice: Subject to any disclaimer, the term of this patent is extended or adjusted under 35 U.S.C. 154(b) by 0 days.

(21) Appl. No.: 10/810,818

(22) Filed: Mar. 29, 2004

(65) Prior Publication Data

US 2004/0208283 A1 Oct. 21, 2004

(30) Foreign Application Priority Data

Apr. 17, 2003 (DE) .............................. 103 17 679

(51) Int. Cl.
*G01N 23/20* (2006.01)
(52) U.S. Cl. .................... 378/70; 378/155; 378/150
(58) Field of Classification Search ............... 378/70, 378/71, 86–89, 147, 148, 150, 151, 34, 84, 378/146, 155
See application file for complete search history.

(56) References Cited

U.S. PATENT DOCUMENTS

| | | | |
|---|---|---|---|
| 3,832,562 A * | 8/1974 | Jacobs et al. | 378/70 |
| 4,950,898 A * | 8/1990 | Fothergill | 250/390.01 |
| 5,050,199 A * | 9/1991 | Watanabe | 378/146 |
| 5,604,353 A | 2/1997 | Gibson | |
| 6,175,609 B1 * | 1/2001 | Edic et al. | 378/7 |

FOREIGN PATENT DOCUMENTS

| | | |
|---|---|---|
| DE | 195 36 822 | 4/1997 |
| WO | WO 00/05 727 | 2/2000 |

OTHER PUBLICATIONS

"ATX-G Optical System". The Rigaku Journal, vol. 16, no. 1, 1999, pp. 53-58.
"Diffraction Solutions für die Materialuntersuchung-D8 Discover", Bruker AXS, pp. 10-15 Apr. 2000.

* cited by examiner

*Primary Examiner*—David V. Bruce
*Assistant Examiner*—Elizabeth Keaney
(74) *Attorney, Agent, or Firm*—Paul Vincent

(57) ABSTRACT

An X-ray optical system comprising an X-ray source (1), from which X-ray radiation (2) is guided to a sample (4) under investigation, and an X-ray detector (7) for receiving radiation (5) diffracted or scattered from the sample (4), wherein a beam-guiding X-ray optical element (3, 6), such as e.g. a collimator, a mono- or polycapillary, an X-ray mirror or a monochromator, is disposed between the source (1) and the sample (4) and/or between the sample (4) and the detector (7), is characterized in that a wobble means is provided for moving the X-ray optical element (3, 6) in an oscillating fashion during the measurement. The inventive X-ray optical system obtains averaged X-ray analysis information from objects under investigation having large mass which consist of macrocrystalline material without destroying or accelerating the object under investigation.

13 Claims, 2 Drawing Sheets

X-RAY OPTICAL SYSTEM WITH WOBBLE DEVICE

This application claims Paris Convention priority of DE 103 17 679.9 filed Apr. 17, 2003 the complete disclosure of which is hereby incorporated by reference.

BACKGROUND OF THE INVENTION

The invention concerns an X-ray optical system with an X-ray source from which X-ray radiation is guided to a sample to be examined, and an X-ray detector for receiving radiation diffracted or scattered from the sample, wherein a beam-guiding X-ray optical element, such as e.g. a collimator, a mono or poly-capillary, an X-ray mirror or a monochromator, is disposed between the source and the sample and/or between the sample and the detector.

X-ray optical systems of this type are realized in almost all conventional X-ray diffractometers, e.g. in "ATX-G optical system", The Rigaku Journal, Vol. 16, No. 1, 1999, pages 53–58.

X-rays are used to examine the material properties of the most different kinds of samples. They can interact with the atoms of the sample in many ways, wherein part of the impinging rays can be scattered or diffracted in sample-specific spatial directions, or the sample itself can be excited to emit radiation. The products of the interaction can give information about the material properties.

X-ray radiation is thereby usually directed onto the sample surface in the form of a highly spatially confined beam. The beam diameter thereby delimits the sample region from which information is obtained and determines the resolution of the overall X-ray optical system. The beam diameter in the region of the sample is between 500 $\mu$m and 50 $\mu$m for typical X-ray diffractometers.

Objects under investigation which comprise crystallites (uniformly scattering regions) having a diameter on the order of magnitude of the beam diameter or larger generate discrete intensity maxima in the diffraction patterns in 3-dimensional angular space. Correspondingly large crystallites can occur e.g. in case of abnormal grain growth in metals, or can also be desired products of a production process. For many methods of X-ray analysis, i.e. a simple theta-2theta scan, these discrete intensity maxima can falsify or even completely eliminate diffraction structures due to the random, irregular orientation distributions of the small number of irradiated crystallites in the sample. This phenomenon, called the grain size effect, is generally undesirable. One rather tries to obtain (locally or globally) averaged information about the sample.

To solve this problem, the sample is conventionally ground into a powder thereby reducing the crystallite size which, however, destroys the object under investigation.

In another conventional method, the position of the object under investigation is changed during the measurement, e.g. with a XYZ positioning table. This produces integral information over a larger sample area. This method is not applicable for many objects under investigation since they cannot be moved at all or only very slowly due to their large mass or high sensitivity to acceleration (e.g. for fluids) and therefore a noticeable increase in the swept sample region in reasonable measuring intervals is not possible.

Departing therefrom, it is the underlying object of the present invention to present an X-ray optical system to obtain averaged information about the material sample through X-ray analysis even for investigation of macrocrystalline objects, without destroying or accelerating the object under investigation.

SUMMARY OF THE INVENTION

This object is achieved in a surprisingly simple but effective fashion with an X-ray optical system of the above-mentioned type by providing a wobble means for moving the X-ray optical element in an oscillating fashion during the measurement.

The oscillating motion of the beam-guiding X-ray optical element changes the region on the sample which provides the information in an oscillating fashion, i.e. it moves on the sample. The information-providing region can be limited by the radiation spot of the impinging X-ray and/or through the scanning region of the detector.

The temporal change of the information-providing region on the sample leads to an effective averaging over the sample region swept (i.e. illuminated or scanned) during a measurement.

If the sample volume illuminated during measurement is large compared to the volume of a crystallite, falsification of the X-ray analysis due to grain size effects is largely eliminated in accordance with the invention.

X-ray optical elements, which are flexible at least at one end, such as glass capillaries or poly capillaries, are particularly suited for the wobble means. The flexible end is connected to the wobble means and faces the sample. The other end faces the X-ray source or the detector.

One preferred embodiment of the inventive X-ray optical system is characterized in that the oscillation frequency of the wobble means is selected such that at least half an oscillation, preferably an integer multiple of half oscillations, is/are carried out during the measurement. For one-dimensional oscillation starting at one of the two edge points, the sweepable sample region is completely taken into consideration during the measurement. Through execution of an integer multiple of half oscillations, every section of the swept sample region is exposed for approximately the same time for averaging, assuming a uniform oscillation speed during oscillation. The oscillation frequency is preferably selected such that exactly one oscillation is carried out during one measurement. In this case, a mechanically gentle, slow oscillation frequency can be selected without having to take into consideration the properly phased starting point of a one-dimensional oscillation.

In a preferred embodiment, the wobble means can effect at least two mutually independent oscillation motions of the X-ray optical element to considerably increase the swept sample region. The two mutually independent oscillation motions are preferably substantially mutually orthogonal, with regard to their effect on the swept sample region.

In a particularly preferred embodiment of the inventive X-ray optical system, the amplitudes of the wobble means can be adjusted such that predetermined, selected sample regions are swept. The predetermined regions may, in particular, be rectangular surfaces or circular surfaces with defined dimensions. In this fashion, the information obtained from an X-ray analysis can be associated with local, defined sample regions.

One embodiment is particularly preferred, with which one wobble means is provided on the side of the source and one wobble means on the side of the detector whose oscillation motions are synchronized. One-sided oscillation motion may violate the Bragg condition which leads to intensity loss in the detector. Synchronized oscillation on the side of the source and also on the side of the detector permits continuous maintenance of the Bragg condition through suitable guiding of a second X-ray optical element to obtain particularly good signal-to-background ratios. The synchronized wobbling is moreover required when the beam spot of the X-ray impinging on the sample and the detection range (scanning range) of the detector are approximately identical. In this case, the beam spot and detecting spot must strictly coincide during oscillation to maintain the intensity on the detector. If, however, the beam spot and detecting spot largely differ in size, wobbling of the smaller spot is sufficient in accordance with the invention.

In one particularly preferred embodiment, the wobble means comprises a piezo element. A piezo element can electronically control small motions in a fast and precise fashion.

Finally, one embodiment of the inventive X-ray optical system is preferred, with which the amplitude of the wobble means is adjusted such that angle changes of the X-ray radiation impinging on the sample or detected by the detector are less than 1°, preferably less or approximately equal to 0.5°. For such an angular deviation from the ideal Bragg position, sufficient X-ray intensity on the detector can generally be expected. The angle change caused by the wobble means is preferably not more than half of the full width at half maximum (FWHM) of a typical X-ray reflection in an X-ray pattern recorded with the X-ray optical system without wobbling.

Further advantages of the invention can be extracted from the description and the drawing. The features mentioned above and below can be used in accordance with the invention individually or collectively in arbitrary combination. The embodiments shown and described are not to be understood as exhaustive enumeration but have exemplary character for describing the invention.

The invention is shown in the drawing and explained in more detail with reference to embodiments.

DESCRIPTION OF THE PREFERRED EMBODIMENT

Figure 1:
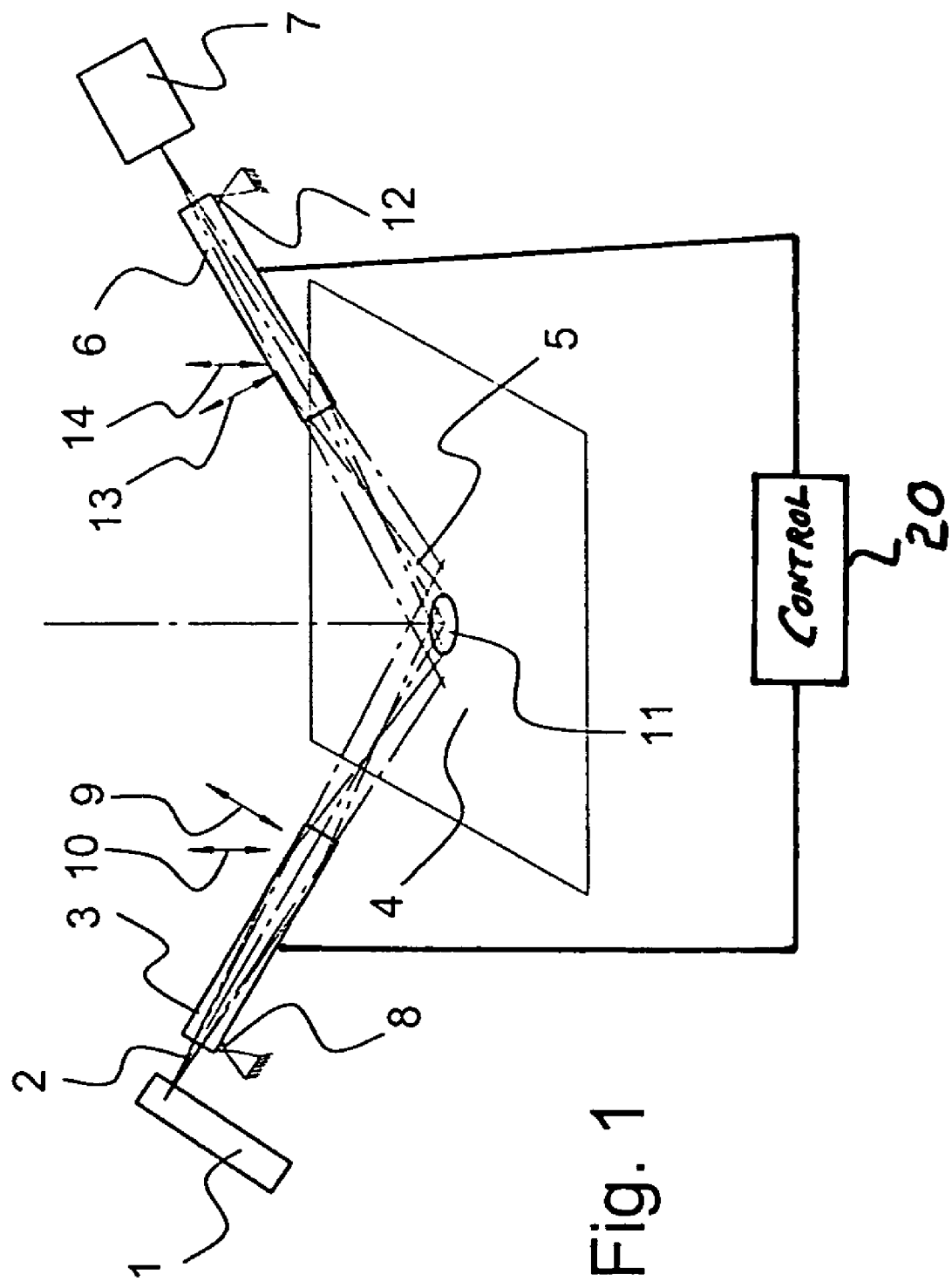
FIG. 1 shows an embodiment of an inventive X-ray optical system in reflection geometry with two wobble means.

FIG. 1 shows a schematic representation of a first embodiment of an inventive X-ray optical system. An X-ray source 1 emits a diverging X-ray beam 2. It is focused by a first X-ray optical element 3, in the present case a monocapillary, and guided to a sample 4. The X-ray beam 2 interacts with the sample 4, and an X-ray beam 5 is emitted. It is focused by a second X-ray optical element 6, which is also formed as monocapillary, and directed onto an X-ray detector 7. The X-ray source 1 and X-ray detector 7 are disposed on one side of the sample 4, which is approximately flat (but must not necessarily be flat). This embodiment is therefore suited for measurements in reflection geometry.

The first X-ray optical element 3 is disposed at its end facing the X-ray source 1 on a ball-and-socket joint 8. The first X-ray optical element 3 can be pivoted ("wobbled") through piezo elements (not shown) in an oscillating fashion in the direction of arrow 9 in the plane of the drawing or also in the direction of arrow 10, perpendicular to the plane of the drawing. The piezo elements and the ball-and-socket joint 8 are thereby the substantial parts of a wobble means which move a beam spot 11 of the impinging X-ray beam 2 on the sample 4. The X-ray source 1 and also the sample 4 and detector 7 remain stationary. The motion of the beam spot 11 on the sample 4 increases the partial region of the sample 4 for measurement which is taken into consideration in a temporally integrated measuring signal of the detector 7.

The second X-ray optical element 6 images X-ray beams 5 emitted from the region of the beam spot 11 onto the detector 7. For this reason, the beam spot 11 and scanning region of the detector 7 on the sample 4 coincide in the illustration shown. To still obtain a useful signal in the detector 7 during oscillation of the beam spot 11 on the sample, the second X-ray optical element 6 must co-oscillate synchronously to the first X-ray optical element 3; i.e. the beam spot 11 and the scanning region of the detector 7 must coincide (overlap). Towards this end, the second X-ray optical element 6 is hinged to a ball-and-socket joint 12 at the end on the detector side. Two piezo elements (not shown) permit pivoting of the second X-ray optical element 6 in an approximately vertical direction in the direction of arrow 13 in the plane of the drawing and in an approximately horizontal direction in the direction of arrow 14, perpendicular to the plane of the drawing.

The piezo elements of the first and second X-ray optical elements 3, 6 are connected to an electronic control 20 which tunes the oscillation between each of the X-ray optical elements 3, 6 and determines the duration of an individual measurement. During an individual measurement i.e. during signal recording on the detector 7 during constant sample, X-ray source and detector position, the X-ray optical elements 3, 6 perform one complete oscillation in each direction of arrows 9, 10, 13, 14 in the embodiment shown.

Figure 2:
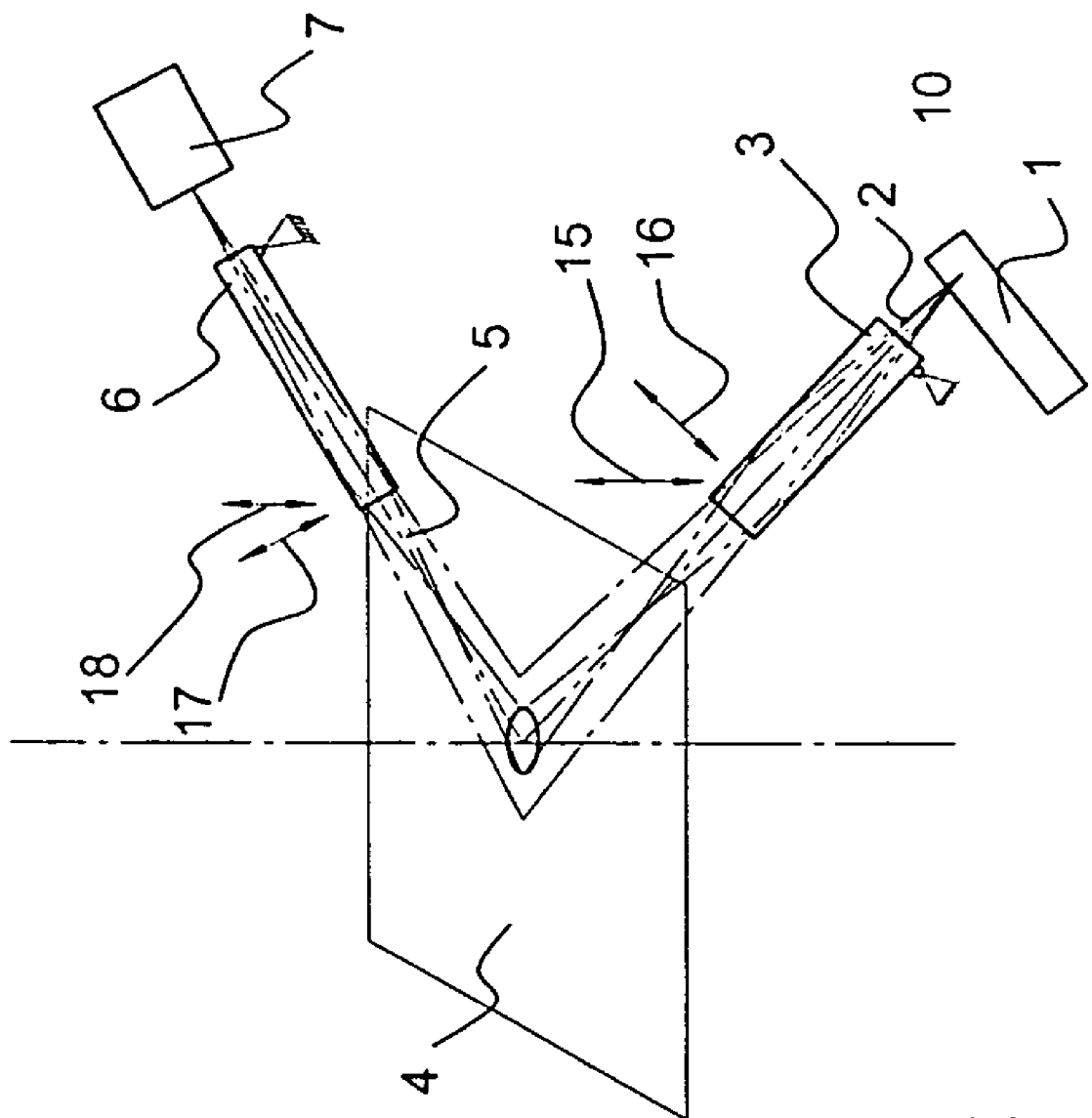
FIG. 2 shows an embodiment of an inventive X-ray optical system in transmission geometry with two wobble means.

FIG. 2 shows an alternative embodiment of the inventive X-ray optical system. In this embodiment, an X-ray source 1 and an X-ray detector 7 are disposed on opposite sides of an (not necessarily) approximately flat sample 4. This embodiment is suited for measurements in transmission geometry.

This embodiment otherwise corresponds to the embodiment of FIG. 1. An X-ray beam 2 which impinges on the sample 4 is focussed by a first X-ray optical element 3. An emitted X-ray beam 5, produced through interaction with the sample 4, is focussed onto the detector 7 by a second X-ray optical element 6. The first X-ray optical element 3 can be wobbled to displace a beam spot on the sample 4 in the direction of arrows 15, 16. The second X-ray optical element 6 can be wobbled to displace the scanning region of the detector 7 on the sample in the direction of arrows 17, 18. Wobbling enlarges the region of the sample 4 providing information during an individual measurement.

We claim:

1. An X-ray optical system for examining a sample, the system comprising:
    an X-ray source from which X-ray radiation is guided to the sample;
    an X-ray detector for receiving radiation from the sample;
    at least one X-ray optical element disposed between said source and the sample and/or between said detector and the sample; and
    wobble means cooperating with said at least one optical element to move said at least one optical element in an oscillating fashion, wherein said wobble means can cause at least two mutually independent oscillations of said X-ray optical element.

2. The system of claim 1, wherein said at least one optical element is at least one of a collimator, a monocapillary, a polycapillary, an X-ray mirror, and a monochromator.

3. The system of claim 1, wherein said X-ray radiation is diffracted or scattered from the sample.

4. The system of claim 1, wherein said wobble means is activated for a measurement of the sample.

5. The system of claim 1, wherein an oscillation frequency of said wobble means is selected such that an integer multiple of half oscillations is performed during one measurement.

6. The system of claim 1, wherein amplitudes of said wobble means can be adjusted to sweep predetermined, selected regions of the sample.

7. The system of claim 1, wherein a first wobble means is disposed on a side of said source and a second wobble means is disposed on a side of said detector, wherein said first and said second wobble means have synchronized oscillation motions.

8. The system of claim 1, wherein said wobble means comprises a motorized drive.

9. The system of claim 1, wherein said wobble means comprises a piezo element.

10. The system of claim 1, wherein an amplitude of said wobble means is adjusted such that angular changes in said X-ray radiation impinging on the sample are less than 1°.

11. The system of claim 1, wherein an amplitude of said wobble means is adjusted such that angular changes in said X-ray radiation detected by said detector are less than 1°.

12. The system of claim 1, wherein an amplitude of said wobble means is adjusted such that angular changes in said X-ray radiation impinging on the sample are less than or approximately equal to 0.5°.

13. The system of claim 1, wherein an amplitude of said wobble means is adjusted such that angular changes in said X-ray radiation detected by said detector are less than or approximately equal to 0.5°.

* * * * *